(12) United States Patent
Karakasa et al.

(10) Patent No.: US 6,740,509 B2
(45) Date of Patent: May 25, 2004

(54) METHOD FOR THE PRODUCTION OF MUCIN-TYPE GLYCOPEPTIDE

(75) Inventors: Ikuko Ishii Karakasa, Sagamihara (JP); Katsumi Ajisaka, Nigata (JP)

(73) Assignee: Ikuko Ishii Karakasa, Sagamihara (JP)

( * ) Notice: Subject to any disclaimer, the term of this patent is extended or adjusted under 35 U.S.C. 154(b) by 0 days.

(21) Appl. No.: 10/155,862

(22) Filed: May 22, 2002

(65) Prior Publication Data

US 2003/0219851 A1 Nov. 27, 2003

(51) Int. Cl.[7] ............... C12P 19/00; C12P 19/44; C12P 9/18; C12N 9/10; C12N 9/40
(52) U.S. Cl. ............... 435/74; 435/72; 435/84; 435/97; 435/193; 435/208; 435/212
(58) Field of Search ............... 435/97, 71.2, 72, 435/74, 84, 193

(56) References Cited

U.S. PATENT DOCUMENTS

| | | | | |
|---|---|---|---|---|
| 5,731,426 A | * | 3/1998 | Smith et al. | 536/23.1 |
| 5,763,598 A | * | 6/1998 | Hamayasu et al. | 536/46 |
| 5,807,943 A | * | 9/1998 | Lee et al. | 526/238.2 |
| 5,955,324 A | * | 9/1999 | Fan et al. | 435/99 |

FOREIGN PATENT DOCUMENTS

| | | |
|---|---|---|
| JP | 01-168283 | 7/1989 |
| JP | 06-016690 | 1/1994 |
| JP | 09-037790 | 2/1997 |
| JP | 2001-046098 | 2/2001 |

OTHER PUBLICATIONS

Ajisaka, et al. "Efficient synthesis of O–linked glycopeptide by a transglycosylation using endo α–N–acetylgalactosaminidase from *streptomyces*sp.", *Biosci. Biotechnol. Biochem.*, (2001) vol. 65(5): 1240–1243.

Ishii–Karakasa, et al. "Partial purification and characterization of an endo α–N–acetylgalactosaminidase from the culture medium of *streptomyces*sp. OH–11242", *Biochem. J.*, (1992) vol. 288: 475–482.

Iwase, et al. "Release of oligosaccharides possessing reducing endo α–N–acetylgalactosaminidase from mucus glycoprotein in *streptomyces*sp. OH–11242 culture medium through action of endo–type glycosidase", *Biochem. Biophys. Res. Com.*, (1988) vol. 151(1): 422–428.

Ishii–Karakasa, et al. "Structural determination of the O–linked sialyl oligosaccharides liberated from fetuin with endo α–N–acetylgalactosaminidase–S by HPLC analysis and 600–MHz $^1$H–NMR spectroscopy", *Eur. J. Biochem.*, (1997) vol. 247: 709–715.

Tanaka, et al. "Screening and fermentation of endo α–N–acetylgalactosaminidase S, a mucin–hydrolyzing enzyme from *streptomyces* acting on the GalNAc–O–Ser (Thr) linkage", *J. of Fermentation and Bioengineering*, (1998) vol. 85(4): 381–387.

* cited by examiner

*Primary Examiner*—Herbert J. Lilling
(74) *Attorney, Agent, or Firm*—Carol L. Francis; Bozicevic, Field & Francis LLP (57) ABSTRACT

Methods for the production of a mucin-type glycopeptide comprising a transglycosylation using a sugar acceptor such as peptide and a sugar donor as an oligosaccharide with an endo-α-N-acetylgalactosaminidase under a given condition is disclosed. The method provides a new practical way to produce mucin-type glycopeptides in industry and can provide an sufficient amount of the mucin-type glycopeptides in a practical use.

16 Claims, 5 Drawing Sheets

METHOD FOR THE PRODUCTION OF MUCIN-TYPE GLYCOPEPTIDE

FIELD OF THE INVENTION

The present invention relates to novel methods for the production of a mucin-type glycopeptide by utilizing a transglycosylation of endo-α-N-acetylgalactosaminidase.

In particular, the present invention relates to the methods for the production of a mucin-type sugar chain adduct of peptide which comprises transferring a liberated sugar chain to a serine residue or a threonine residue of the peptide or protein as a sugar acceptor in the presence of the sugar acceptor of high concentration by an endo-α-N-acetylgalactosaminidase, instead of the original use thereof to hydrolyze the sugar chain.

BACKGROUND OF THE INVENTION

It has been found that a sugar chain combined with a glycopeptide or a glycoprotein functions in interactions among cells and enhances a resistance of the glycopeptide or the glycoprotein to a protease. Therefore various technologies of combining a sugar chain with a peptide or a protein have been developed in order to develop, for example, peptidic medicaments having high effects.

For example, there has been known a method for combining a complex-type sugar chain or a mannose-rich sugar chain with a peptide or a protein comprising, by utilizing a transfer reaction of endo-β-D-N-acetylglucosaminidase, cleaving the complex-type sugar chain or the mannose-rich sugar chain between GlcNAc-GlcNAc of the three sugar base core; and then transferring the sugar chain of nonreducing end upward of the cleaving site to GlcNAc residue of the peptide or the protein.

However there has not been found an endo-type enzyme which can be used in the production of a mucin-type sugar chain adduct of peptide or protein. Although there has been known in the art an endo-α-D-N-acetylgalactosaminidase capable of liberating a mucin-type sugar chain from the mucin-type sugar chain adduct of peptide or protein, a transfer reaction that the sugar chain is transferred to the peptide has not been reported. For example, R. M. Bardales and V. P. Bhavanandan reported that an endo-α-D-N-acetylgalactosaminidase from *Diplococcus pneumoniae* transfers sugar chains of glycopeptides obtained by decomposing a protein to glycerol, serine or threonine, but did not report an activity of transferring the sugar chains to a peptide or a protein (J. Biol. Chem. Vol. 264, 19893–19897 (1989)).

Accordingly, in order to synthesize a mucin-type glycopeptide, there was a need to use a chemical synthesis method by C. M. Taylor (Tetrahedron, 54, 11317–11382 (1998)) or a chemoenzymatic method by K. Ajisaka and M. Miyasato (Biosci. Biotechnol. Biochem., 64, 1743–1746 (2000)). However these methods are inappropriate to apply in an industrial manufacturing. The chemical method needs many steps for the protection and deprotection of hydroxyl groups in the carbohydrate moiety and amino- or carboxyl groups in the peptide moiety. The chemoenzymatic method recently developed also includes synthesizing at first a GalNAc-linked peptide by a peptide synthesizer using per-acetylated GalNAc-linked Fmoc serine derivative. The GalNAc-linked serine residue was very labile for recemization, especially during the deacetylation reaction with sodium methoxide in dry methanol. Moreover, the yield of the following enzymatic galactosylation or sialylation for the extension of sugar chain depends on the solubility of the glycopeptide used as an acceptor of transglycosylation. Therefore an industrially advantageous method for the production of mucin-type glycopeptides was not known in the art.

In view of industrially manufacturing the mucin-type glycopeptides, a method for the production thereof by combining a whole sugar chain with a peptide utilizing an endo-type enzyme is most appropriate among various methods for the synthesis of glycopeptides. An object of the present invention is to utilize an endo-α-N-acetylgalactosaminidase having activities to liberate a mucin-type sugar chain in the endo-type form and to transfer the liberated sugar chain to a hydroxyl group of serine residue or threonine residue of another peptide or protein to accomplish a method for the production of glycopeptide.

It had been reported that endo-α-N-acetylgalactosaminidases had an activity to hydrolyze the mucin-type sugar chain (Y. Tanaka, Y. Takahashi, M. Shinose, S. Omura, I. I. -Karakasa, H. Iwase and K. Hotta, J. Fermentation and bioengineering, Vol. 85, 381–387 (1998)). The inventors has further found out in their study that some endo-α-N-acetylgalactosaminidases from microorganisms in particular, those belonging to the genus, Streptomyces, have an ability to transfer a mucin-type sugar chain with a glycosidic linkage to a peptide or a protein, in addition to the activity to hydrolyze the mucin-type sugar chain. The inventors have accomplished the present invention based on this finding.

SUMMARY OF THE INVENTION

The present invention provides a method for the production of mucin-type glycopeptide comprising a transglycosylation using a sugar donor and a sugar acceptor with an endo-α-N-acetylgalactosaminidase.

More particularly, the present invention provides a method for the production of a mucin-type sugar chain adduct of peptide comprising the steps of providing a glycoside compound having a mucin-type sugar chain as a sugar donor and a peptide containing threonine residue(s) or serine residue(s) as a sugar acceptor; and applying an endo-α-N-acetylgalactosaminidase to the glycoside compound and the peptide, transferring the mucin-type sugar chain of the glycoside compound to the serine residue or the threonine residue of the peptide to produce the mucin-type sugar chain adduct of peptide.

DETAILED DESCRIPTION OF THE INVENTION

Definitions and Abbreviations:

The term "peptide" used herein means a peptide comprising two or more amino acids, an oligo peptide, a polypeptide or a protein.

The term "glycopeptide" used herein means a glycopeptide or a glycoprotein.

The following abbreviations are used: "endo-α-GalNAc-ase" means endo-α-N-acetylgalactosaminidase. "NMR" means nuclear magnetic resonance spectrum. MS stands for mass spectrum. "%" is percent by weight, unless corresponding concentrations are indicated in other units. Temperatures are given in degrees Celsius.

General:

The endo-α-GalNAc-ase used for the present invention may be an endo-α-GalNAc-ase derived from any organisms as long as it can transfer a mucin-type sugar chain from a sugar donor to a sugar acceptor. It is preferably derived from a microorganism belonging to the genus, Diplococcus, Alcaligenes or Streptomyces, and more preferably belonging to the genus, Streptomyces. In particular, it is preferably derived from a microorganism selected from the group consisting of *Diplococcus pneumoniae*, Alcaligenes sp. and Streptomyces sp, and more preferably, Streptomyces sp. The microorganism to be used may be wild strains, variants, or recombinant strains produced by genetic techniques such as cell fusion or gene manipulation.

The endo-α-GalNAc-ases useful for the present invention are disclosed in pre-granted publication of JP application No. H01-168283. The endo-α-GalNAc-ases were produced by Streptomyces sp. designated as O11-11242 and deposited at the National Institute of Bioscience and Human-Technology, also known as the International Patent Orgaism Depository (IPOD), Agency of Industrial Science and Technology (AIST) in Japan, located at AIST Tsukuba Central 61-1, Higashi 1-chome Tsukuba-shi, Ibaraki-Ken 305-8566 Japan, under accession number FERM P-9243, which is available from the National Institute.

The preferred endo-α-GalNAc-ase of the present invention described in JP-A No. H01-168283 has the following physicochemical properties:

(a) Action: acting on a p-nitrophenyl-α-N-acetylgalactosamine having a alpha-glycoside bond, to release N-acetylgalactosamine and acting on a mucin to release an oligosaccharide having at least two monosaccharides and N-acetylgalactosamine at reducing end;

(b) Optimum pH: optimally active at a pH of about 5 to about 6 when reacted at 37 degree Celsius;

(c) pH Stability: most stable at a pH of about 5.5 and having more than 50% of the maximum activity at a pH ranging from 4.5 to 8.0;

(d) Optimum temperature: optimally active at a temperature ranging from 35 to 40 degree Celsius in a thirty minute reaction and retaining more than 50% of the maximum activity at a temperature ranging from 35 to 55 degree Celsius;

(e) Thermostability: stable at less than 40 degree Celsius;

(f) Molecular weight: about 105,000 determined by gel filtration using Sephadex G-200;

(g) Effects of metal ions and substances: no activity inhibition by $Ca^{2+}$, $Mg^{2+}$, and $Mn^{2+}$ and by EDTA but activity inhibition by PCMB.

The endo-α-GalNAc-ases of the present invention can be recovered and purified from cell cultures of microorganisms described above by conventional methods, for example, including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

In the transfer reaction of the present invention, the sugar donors may include a naturally occurring oligosaccharide such as glycopeptide, glycoprotein and/or oligosaccharide derivative or a non-naturally occurring oligosaccharide as long as the oligosaccharides have sugar chains which can be hydrolyzed by the endo-α-GalNAc-ase of the present invention. Namely, the sugar donors include glycoside compounds having the sugar chain of core 1 to 5 type such as Galβ1-3GalNAc residue, NeuAcα2-3Galβ1-3GalNAc residue, Galβ1-3(GlcNAβ1-6)GalNAc residue, GlcNAcβ1-3GalNAc residue, GalNAcα1-3GalNAc residue, GlcNAcβ1-3(GlcNAcβ1-6)GalNAc residue, NeuAcα2-6GalNAc residue and the like, combining therewith the aglycon such as saccharide, peptide, protein, lipid, alcohol or phenol.

The sugar chains as a synthesized sugar chain include Galβ1-3GalNAc-α-pNP in which the galactose is combined with para-nitrophenyl-α-D-N-acetylgalactosamine (GalNAcα-pNP) by β1-3 bond, or the oligosaccharide having an extended sugar chain. An aglycon moiety of the synthesized sugar chain is not limited to para-nitrophenyl group but further include any aryl or alkyl which may be used to form a glycosidic bond in a typical process of a saccharide chemistory such as orto-nitrophenyl, benzyl or methyl.

Where a naturally occurring mucin-type sugar chain is used as a sugar donor, a glycoprotein may be used without any modification but the use of a mixture of glycopeptides obtained by hydrolyzing the glycoprotein with a protease or an acid accelerates the reaction of the present invention. In this case, although simple sugar chains may not be provided due to the microheterogeneity of the sugar chains, it would not affect the reaction.

The sugar acceptors of the present invention include peptides which are not limited due to their structures as long as the peptides include a serine residue or a threonine residue. The sugar acceptors also include proteins in addition to the peptide. Where the proteins are used as a sugar acceptor, the serine residue or the threonine residue of the protein to which the sugar chains are transferred cannot be designated, that is, the sugar chains are transferred to the serine residues or the threonine residues in the protein at random.

Where a sugar or a sugar chain of the sugar donor is transferred to a peptide by utilizing a transfer ability of hydrolase such as endo-α-N-acetylgalactosaminidase, a higher concentration of the sugar donor is preferable, though the concentration is restricted due to its solubility. The concentration generally ranges from about 1.0 to about 70%, preferably ranges from about 2.0 to about 20%, more preferably ranges from about 3 to about 10%. If the concentration is lower than 1.0%, a yield of the resultant glycopeptide extremely decreases and the hydrolase is normally unpractical in the transfer reaction because the hydrolase decomposes the sugar donor strongly rather than transfers the sugar chain. Although the concentration can be over 70%, it is preferable to adopt the concentration of less than 70% since a high concentration solution tends to have a high viscosity and causes the precipitation.

A concentration of the sugar acceptor largely affects a yield of the resulting product. In view of the viscosity of solution and the precipitation of the sugar donor, it is preferable to adopt the concentration of less than 70%, although the higher concentration can be usable. The concentration of the sugar acceptor generally ranges from about 1.0 to about 70%, preferably ranges from about 2.0 to about 20%, more preferably ranges from about 3 to about 10%.

In addition, although a ratio of the sugar donor to the sugar acceptor is an important factor in calculating the yield of the resulting product, the more valuable one should be used in the reduced concentration after comparing the sugar donor with the sugar acceptor in a commercial value.

The ratio may range from 0.1 to 10. If the peptide is more valuable that the sugar donor, the sugar donor may be used about two to ten times in mole as much as the peptide used in the transfer reaction, preferably from two to five times and more preferably from two to three times. In contrast, if the sugar donor is more valuable than the peptide as a sugar acceptor, the peptide may be used about two to ten times in mole as much as the sugar donor used in the transfer reaction, preferably from two to five times and more preferably from two to three times.

The reaction of the present invention can be conducted at 35 to 55 degree Celsius, preferably 35 to 40 degree Celsius, and at pH 4.5 to 8.0, preferably about 5 to 6. The reaction time is determined based on quantities of the sugar donor, the sugar acceptor and the endo-α-GalNAc-ase and generally ranges from 1 to 24 hours, preferably 1 to 2 hours. The reaction medium to be used includes water, a buffer, and an aqueous organic solvent such as alcohols.

The glycopeptides obtained by the addition of mucin-type sugar chains according to the present invention indicate an highly enhanced resistance against three proteases having been tested. Consequently, the method for the addition of mucin-type sugar chains according to the present invention obviously and largely contributes a functional improvement of peptidic medicaments.

The present invention is further explained in detail by the following examples which should not be construed as limiting the scope of the invention.

EXAMPLES

Example 1

Preparation of Endo-α-N-Acetylgalactosaminidase

The endo-α-N-acetylgalactosaminidase used in the working examples herein below were prepared according to the method described in Y. Tanaka, I. I. -karakasa et. al, J. Fermentation and Bioengineering, Vol. 85, 381–387 (1998).

Streptomyces sp. OH-11242 having accession number FERM P-9243 was used to produce the endo-α-N-acetylgalactosaminidase. Spores and Mycelia of the strain OH-11242 were inoculated into a 500 ml culture flask containing 100 ml of seed medium consisting of 2% (w/v) glucose, 0.5% (w/v) peptone, 0.5% (v/v) meat extract, 0.3% (w/v) dry yeast cells, 0.5% (w/v) NaCl, and 0.3% (w/v) $CaCO_3$, at pH 7.0. This system was incubated with shaking at 27 degree Celsius for 2 days. The seed culture (4 ml) obtained was transferred to a 500 ml culture flask. Each flask contained 100 ml of production medium consisting of 0.26% (w/v) ammonium sulphate, 0.24% $KH_2PO_4$, 0.43% (w/v) $K_2HPO_4$, 0.10% (w/v) $MgSO_4$, $7H_2O$, 0.1% (v/v) trace metal solution, and 0.5 g of PGM (pig gastric mucin), at pH 7.0. A trace metal solution, adjusted to pH 7.0 by NaOH, consisted of 0.64% (w/v) $CuSO_4$, $5H_2O$, 0.11% (w/v) $FeSO_4$, $7H_2O$, 0.79% (w/v) $MnCl_2$, $4H_2O$, 0.15% (w/v) $ZnSO_4$, $7H_2O$ and distilled water. The flasks were incubated at 27 degree Celsius for 3 days with reciprocal shaking (120 strokes/min).

The culture fluid of Streptomyces sp. OH-11242 was dialysed against distilled water. The dialysate was brought to 80% saturation by adding solid ammonium sulphate with stirring. The precipitate thus formed was collected by centrifugation at 9,500 g for 20 minutes, dissolved in a minimum amount of water and dialysed against distilled water. By this process, the endo-α-GalNAc-ase was prepared.

For the determination of the endo-α-GalNAc-ase-S activity, one mg of pig gastric mucus glycoprotein (PGM) was incubated with 50 µl of enzyme solution and an appropriate amount of buffer, in a total volume of 200 µl. After incubation at 37 degree Celsius for 17 hours, the reaction mixture was boiled at 100 degree Celsius for 10 minutes and precipitated by ethanol [final concentration 80%]. Following centrifugation at 6,000 g for five minutes, the supernatant was used for the following experiment.

A portion of the solution was analyzed for oligosaccharide content by thin layer chromatography (TLC). The other oligosaccharides in the solution were pyridylaminated (PA) and chromatographed on a gel-filtration column (TSK-GEL G2000PW) to obtain oligosaccharides larger than Galβ1-3GalNAc. The fraction of oligosaccharides-PAs which were larger than Galβ1-3GalNAc-PA was collected and concentrated to dryness. To determine the reducing terminal sugars of oligosaccharides liberated from PGM through enzyme reactions, oligosaccharide-PA was hydrolysed with 4M HCl at 100 degree Celsius for six hours in a sealed tube, and the pyridylaminated monosaccharides produced were chromatographed on a reversed-phase column following re-acetylation of the amino groups.

To simplify the calculation of the endo-α-GalNAc-ase-S activity, one unit thereof is defined as the amount of enzyme which can liberate one µmol of para-nitrophenol per minute by using Galβ1-3GalNAcα-pNP as a substrate. The enzyme activity of the endo-α-GalNAc-ase was 32.5 unites/ml.

Example 2

Preparation of Glycopeptide Having Mucin-Type Sugar Chains

Figure 1:
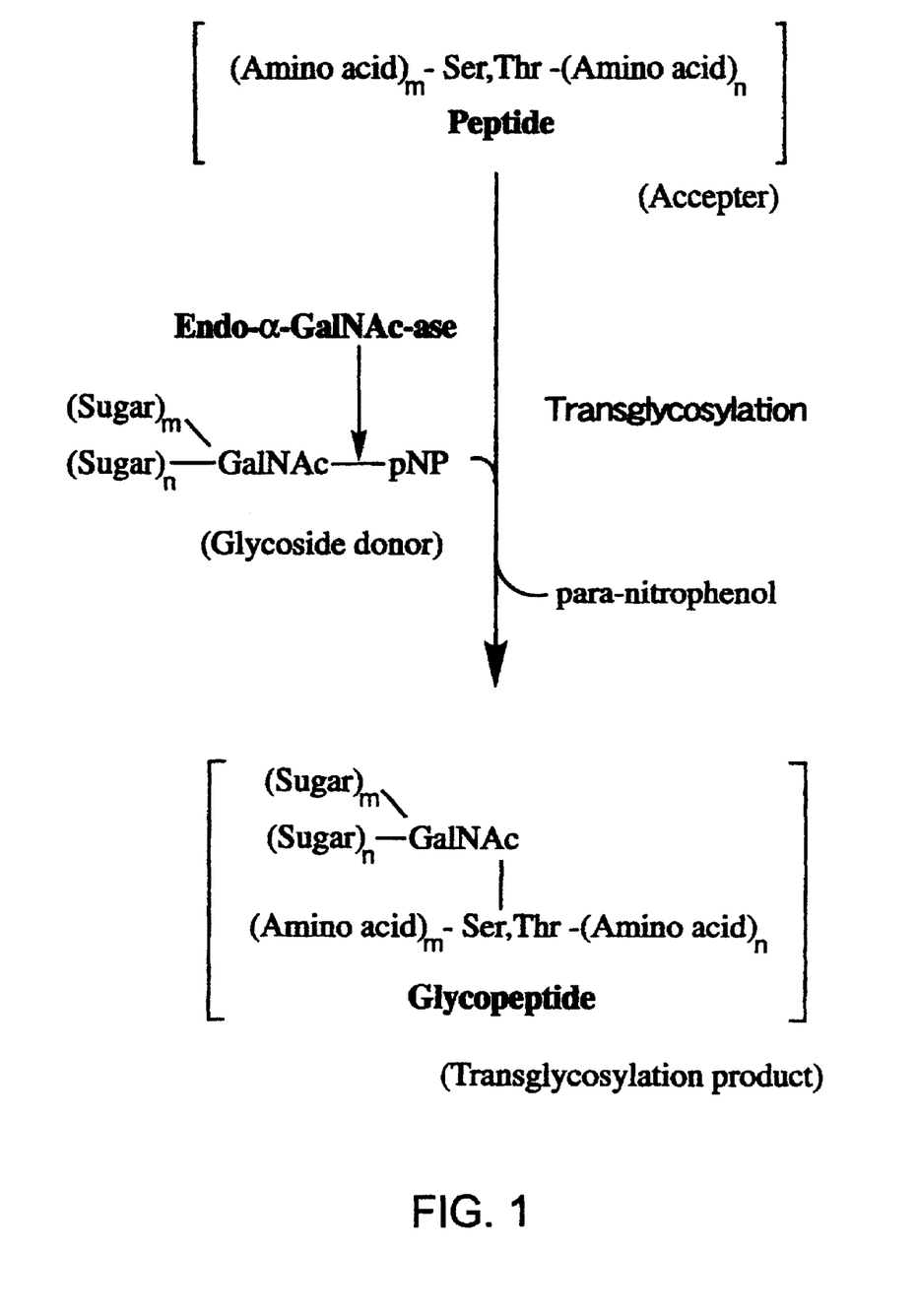
FIG. 1 depicts a schematic representation of enzymatical synthesis of the present invention.

The synthesis of a glycopeptide using the transfer activity of endo-α-GalNAc-ase-S was conducted with fibroblast growth factor (FGF)-fragment peptide (Leu-Ser-Gln-Val-His-Arg) as a sugar acceptor and Galβ1-3GalNAcα-pNP as a sugar donor. This process is illustrated in the scheme of FIG. 1.

Figure 3:
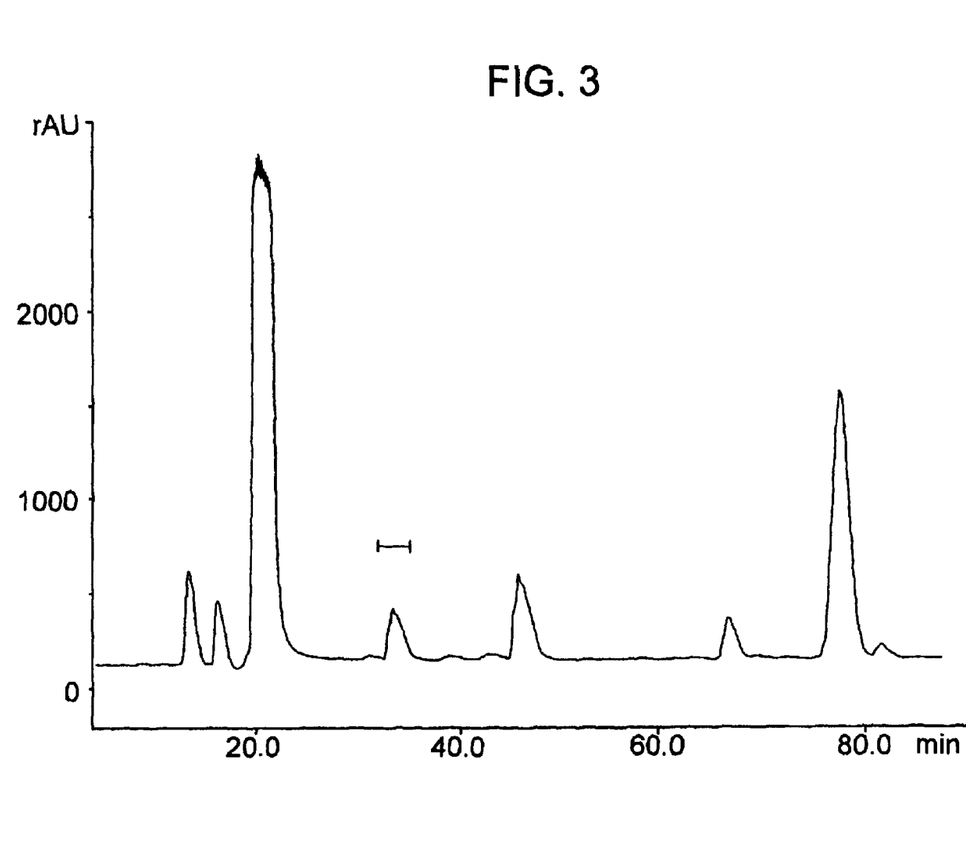
FIG. 3 depicts the result of fractionation of reactants in the method of the present invention by HPLC using a device of Pharmacia Acta Purifier. The column and elution conditions are described in Example 1.

Benzyloxycarbonyl (Cbz)-linked FGF-fragment was synthesized by peptide synthesizer without any modification except for the use of a Cbz-Leu cartlidge instead of an Fmoc-Leu cartlidge for the N-terminal. Galβ1-3GalNAcα-pNP (21.1 mg) and Cbz-linked FGF-fragment hexapeptide (10.0 mg) were dissolved in 250 µl of 0.1M sodium acetate buffer (pH 5.2) containing 10% DMF and 50 µl of partially purfied endo-GalNAc-ase-S (31.3 units/ml) was added to the mixture. The mixture was incubated at 37 degree Celsius for two hours and the reverse phase HPLC was measured at appropriate times by the detection using UV of 215 nm. A representative HPLC chart is shown in FIG. 3. The enzyme was deactivated by heating at 100 degree Celsius for five minutes.

The reaction mixture was put on preparative HPLC column (Mightysil RP-18, Kanto Chemicals Co., Tokyo, Japan, 3.5 cmΦ×25 cm) and eluted with a gradient of 10%→50% acetonitrile (120 min, 10 ml/min) containing 0.1% trifluoroacetic acid. 1.5 mg of Galβ1-3GalNAc-linked hexapeptide was obtained by the concentration of fragment marked in FIG. 3 (yield; 11% based on the acceptor).

Figure 4:
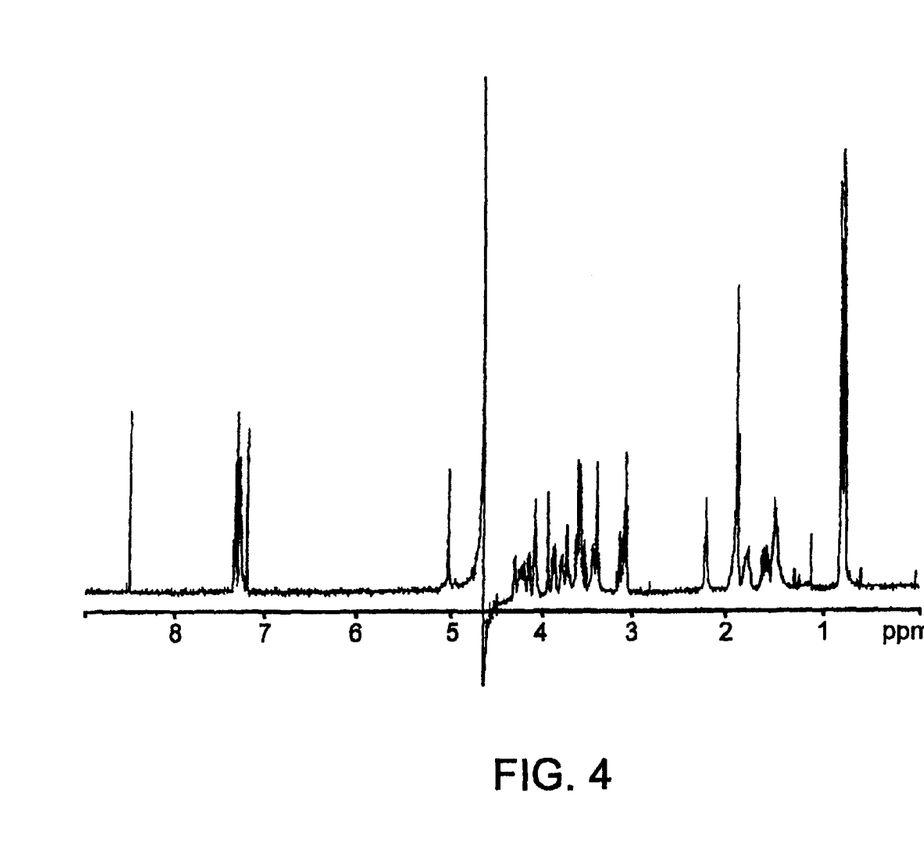
FIG. 4 depicts 1H NMR spectrum (500 MHz, D2O) of the product of the present invention. Varian Inova 500 was used in this determination.

1H-NMR data (500 MHz, $D_2O$)-δ (FIG. 4): 1.898 (s, 3H, N-Ac(GalNAc)); 3.073 (t, 3J (H,H)=7.14 Hz, 2H, H β (His)); 3.435 (broad s, 1H, H-5 (GalNAc)); 3.735 (broad s, 1H, H-4 (GalNAc)); 3.79 (broad s, 1H, H-5 (Gal)); 3.880 (broad d, 3J (H,H)=10.51 Hz, 1H, H-3 (GalNAc)); 3.951 (d, 3J (H,H)=7.80 Hz, 1H, Hα (Val)); 4.210 (dd, 3J (HH)=3.34 Hz, 10.59 Hz, 1H, H-2 (GalNAc)); 4.251 (dd, 3J (H,H)=5.57 Hz, 8.08 Hz, 1H, H α (Arg)); 4.229 (d, 3J (H,H)=7.25 Hz, 1H, H-1 (Gal)); 4.791 (d, 3J (H,H)=4.09 Hz, H-1 (GalNAc)); 7.214 (s, 1H); 8.494 (s, 1H). TOF-MS: calcd. for [M+H], 1238.6; found, 1239.3; calcd. for [M+Na], 1260.6; found, 1261.5.

Figure 2:
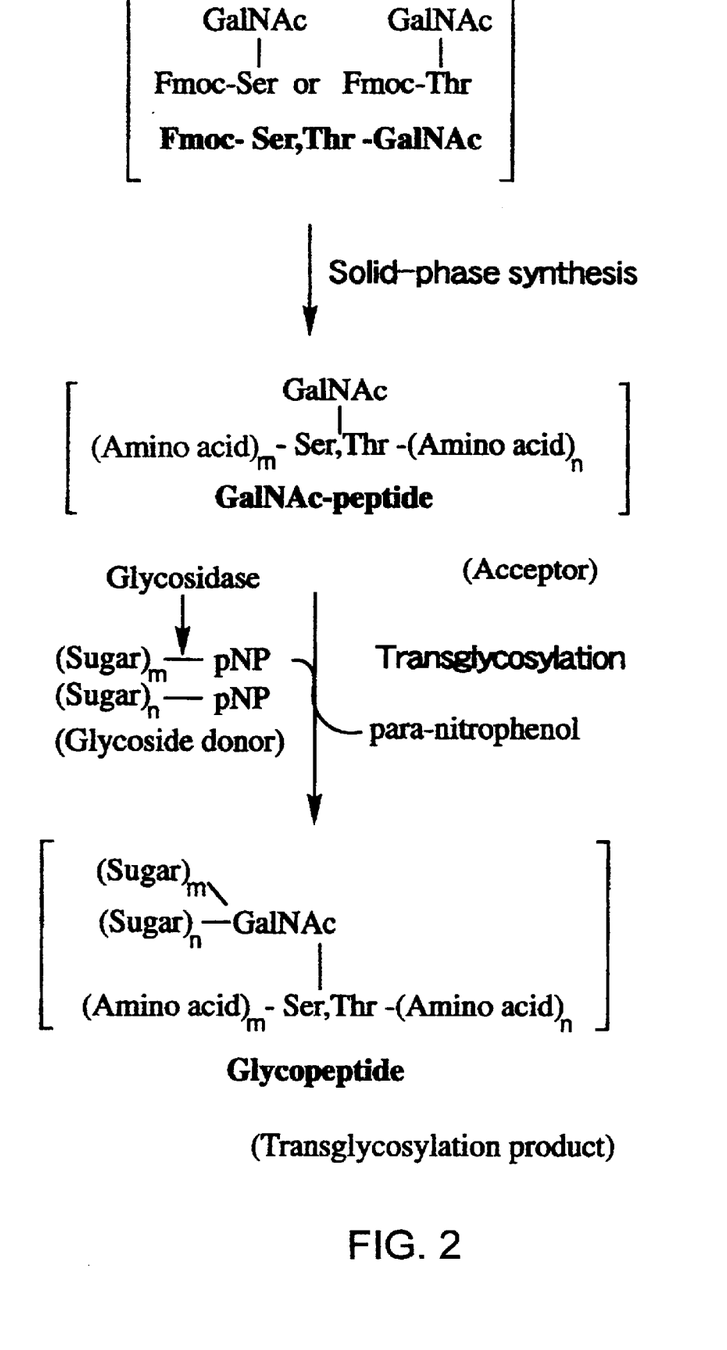
FIG. 2 depicts a schematic representation of Chemo-enzymatic synthesis of the conventional technology.

In order to confirm the structure of the resultant product, Galβ1-3GalNAc-linked hexapeptide was synthesized by a chemoenzymatic method illustrated in FIG. 2. At first, GalNAc-linked hexapeptide was synthesized using peptide synthesizer. Cartridges containing 0.1 mmoles of Cbz-Leu and other Fmoc amino acids were placed together with 0.025 mmole of peracetylated GalNAc-linked Fmoc-Ser on the peptide synthesizer and peptide synthesis was done by the normal mode. After deprotection, the deacetylation was completed by stirring the acetylated glycopeptide in the 0.01M Sodium methoxide solution at 0 degree Celsius for 1 hour. By the purification with preparative reverse phase HPLC, 80 mg of GalNAc-linked hexapeputide was obtained (yield; 30%). As the second step, Galβ-pNP (70 mg) and GalNAc-hexapeptide (50 mg) were dissolved in 430 μl of 0.1M phosphate buffer (pH 6.0) containing 10% DMF. After the addition of 70 μl of β-galactosidase from *Bacillus circulans* (25 units/mL), the solution was incubated at 37 degree Celsius for 6 hours. The solution was heated in a boiling water bath for 3 min and 7.4 mg of the product (yield; 13% based on the acceptor) was isolated by the use of the preparative reverse phase HPLC column. The β1-3-linked structure was confirmed by the downfield shift of C-3 of GalNAc residue from 68.9 ppm to 77.5 ppm in the two-dimensional $^{13}C$-$^1H$ correlation spectrum.

The 1H-NMR spectra of both glycopeptide synthesized by different methods coincided completely and the two glycopeptides were confirmed to be the same.

In the conventional method illustrated in FIG. 2, the total yield of the disaccharide-hexapeptide was about 4% with two steps. In contrast, the yield was about 10% in this working example with two steps (synthesis of unglycolated peptide and transglycosylation). Although an expensive peracetylated GalNAc-linked Fmoc-serine must be used for the synthesis of GalNAc-linked peptide in the first step of the conventional method, normal unglycosylated peptide can be used as a sugar acceptor in the present invention. Moreover in the present invention, the sugar donor, Galβ1-3GalNAcα-pNP, can be easily prepared from Galβ-pNP and GalNAcα-pNP by transglycosylation using β-galactosidase from *B. circulans* (recombinant). This method can be used for the synthesis of the sialylated glycopeptide by the use of NeuAcα2-3Galβ1-3GalNAcα-pNP which can be easily prepared by transglycosylation using sialidase. If one would like to synthesize it via the conventional method, expensive CMP-NeuAc and sialyltransferase must be used for the sialylation of Galβ1-3GalNAc linked hexapeptide. Therefore it is apparent that the present invention is more advantageous than the conventional method.

Example 3

Preparation of Glycopeptide Having Mucin-Type Sugar Chains

The synthesis of a glycopeptide using the transfer activity of endo-α-GalNAc-ase-S was conducted with Bradykinin (Arg-Pro-Pro-Gly-Phe-Ser-Pro-Phe-Arg) as a sugar acceptor and Galβ1-3GalNAcα-$CH_2C_6H_5$ as a sugar donor.

10.08 mg Of Bradykinin and 20 mg of Galβ1-3GalNAcα-$CH_2C_6H_5$ were dissolved in 310 μl of 0.1M acetate buffer (pH 5.2) containing 10% DMF. 40 μl (1.3 unit) Of partially purified endo-GalNAc-ase-S was added to the mixture. The mixture was incubated at 37 degree Celsius for two hours and the reverse phase HPLC was measured at appropriate times by the detection using UV of 215 nm. The enzyme was deactivated by heating at 100 degree Celsius for five minutes.

Figure 5:
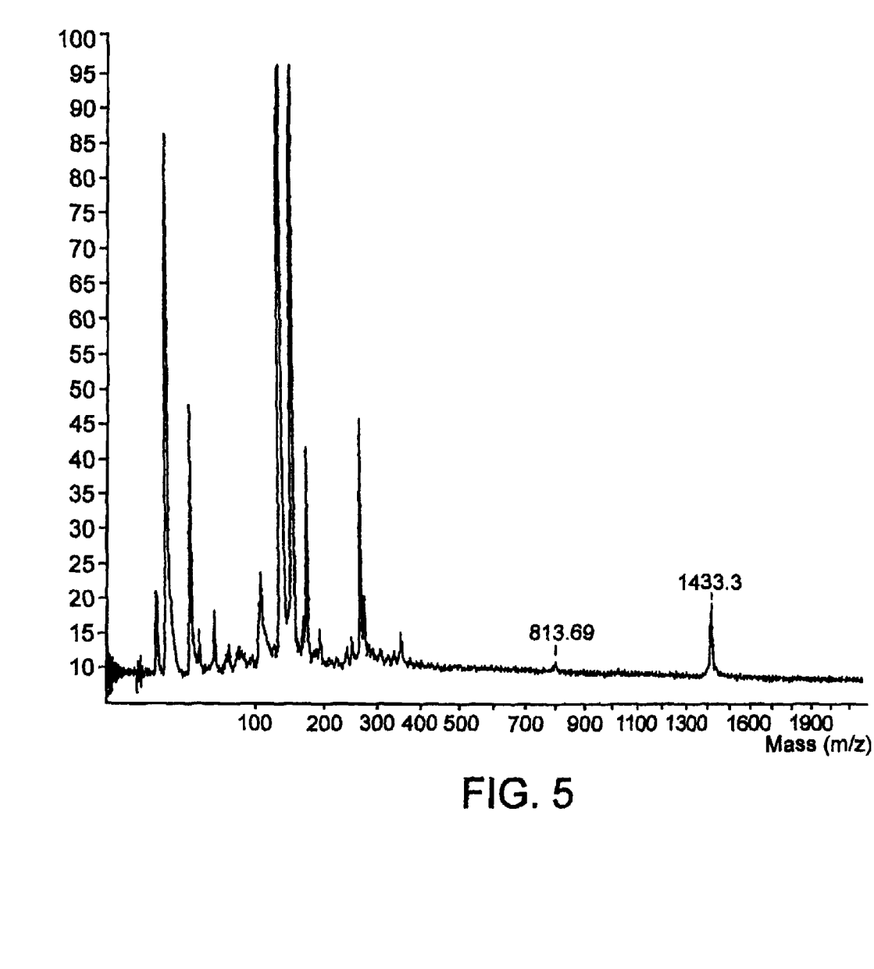
FIG. 5 depicts a spectrum of a disaccharide adduct of bradykinin measured by time-of-flight mass spectrometer (Laser mat 2000 produced by Bioanalysis Inc.). 2,5-Dihydroxybenzoic acid was used as a matrix.

The reaction mixture was put on preparative HPLC column (Mightysil RP-18, Kanto Chemicals Co., Tokyo, Japan, 3.5 cmΦ×25 cm) and eluted with a gradient of 10%→50% acetonitrile (120 min, 10 ml/min) containing 0.1% trifluoroacetic acid. 1.0 mg of the desired disaccharide adduct of Bradykinin was obtained. FIG. 5 shows a spectrum of the adduct measured by time-of-flight mass spectrometer. The peak of m/s 1433.3 is a peak corresponding to [M+H] of the peptide in which Galβ1-3GalNAc was adducted to Bradykinin.

Example 4

Measurement of the Glycopeptides' Resistance Against Proteases

In order to compare the resistance against a protease of the hexapeptide synthesized in example 1 to which Galβ1-3GalNAc was adducted and the resistance of the peptide (Cbz-Leu-Ser-Gln-Val-His-Arg) having no sugar chain, a comparative experiment therefor was conducted.

100 μl of 1 mM each sample solution was mixed with 100 μl of 20 mU protease solution (Luecine amino peptidase, Proteinase K and Protease type III) and each mixture was incubated at 37 degree Celsius. The peak heights were chronologically measured by HPLC. As a result, it was found that the peptide having no sugar chain was completely hydrolyzed in one hour by each of all the three proteases. In contrast, 100% of Galβ1-3GalNAc adduct of the peptide was retained where Luecine amino peptidase and Proteinase K was used to hydrolyze, and 96% thereof was retained where Protease type III was used. Accordingly, it has been confirmed that the glycopeptides to which a sugar chain was adducted according to the present invention have a strong resistance against the hydrolyzation by protease. A high utility thereof is expected in an industrial field.

What is claimed is:

1. A method for the production of mucin-type glycopeptide comprising a transglycosylation using a sugar donor and a sugar acceptor with an endo-α-N-acetylgalactosaminidase wherein the endo-α-N acetylgalactosaminidase is produced by a microorganism which is a Streptomyces spp.

2. The method of claim 1 wherein the microorganism is Streptomyces sp. OH-11242 having accession number FERM BP-9243.

3. A method for the production of mucin-type glycopeptide comprising a transglycosylation using a sugar donor and a sugar acceptor with an endo-α-N-acetylgalactosaminidase wherein the endo-α-N-acetylgalactosaminidase is produced by a microorganism which is a Streptomyces spp., and further wherein the endo-α-N-acetylgalactosaminidase has the following physicochemical properties:
(a) Action: acting on p-nitrophenyl-alpha-N acetylgalactosamine having an alpha-glycoside bond, to release N-acetylgalactosamine and acting on a mucin to release an oligosaccharide having at least two monosaccharides and N-acetylgalactosamine at reducing end;

(b) Optimum pH: optimally active at a pH of about 5 to about 6;

(c) pH Stability: most stable at a pH of about 5.5;

(d) Optimum temperature: optimally active at a temperature ranging from 35 to 40 degree Celsius in a thirty minute reaction;

(e) Molecular weight: about 105,000 determined by gel filtration using Sephadex G-200.

4. The method of claim 1 wherein the sugar donor is selected from the group consisting of alkylglycoside and arylglycoside.

5. The method of claim 4 wherein the sugar donor is the glycoside having a member, as an aglycon, selected from the group consisting of para-nitrophenyl, ortho-nitrophenyl and benzyl.

6. The method of claim 1 wherein the sugar donor comprises a mixture of glycopeptides prepared by hydrolyzing a glycoprotein containing a mucin-type sugar chain.

7. The method of claim 1 wherein the sugar acceptor is a peptide containing serine residue or threonine residue.

8. A method for the production of mucin-type glycopeptide comprising a transglycosylation using a sugar donor and a sugar acceptor with an endo-α-N-acetylgalactosaminidase wherein the endo-α-N acetylgalactosaminidase is produced by a microorganism which is a Streptomyces spp., and further wherein the endo-α-N-acetylgalactosaminidase has the following physicochemical properties:

(a) Action: acting on p-nitrophenyl-alpha-N acetylgalactosamine having an alpha-glycoside bond, to release N-acetylgalactosamine and acting on a mucin to release an oligosaccharide having at least two monosaccharides and N-acetylgalactosamine at reducing end;

(b) Optimum pH: optimally active at a pH of about 5 to about 6 when reacted at 37 degree Celsius;

(c) pH Stability: most stable at a pH of about 5.5 and having more than 50% of the maximum activity at a pH ranging from 4.5 to 8.0;

(d) Optimum temperature: optimally active at a temperature ranging from 35 to 40 degree Celsius in a thirty minute reaction and retaining more than 50% of the maximum activity at a temperature ranging from 35 to 55 degree Celsius;

(e) Thermostability: stable at less than 40 degree Celsius;

(f) Molecular weight: about 105,000 determined by gel filtration using Sephadex G-200;

(g) Effects of metal ions and substances: no activity inhibition by $Ca^{2+}$, $Mg^{2+}$, and $Mn^{2+}$ and by EDTA but activity inhibition by PCMB.

9. The method of claim 8 wherein the sugar donor is selected from the group consisting alkylglycoside and arylglycoside.

10. The method of claim 9 wherein the sugar donor is the glycoside having a member, as an aglycon, selected from the group consisting of para-itropheyl, ortho-nitrophenyl and benzyl.

11. The method of claim 8 wherein the sugar fonor comprises a mixture of glycopeptides prepared by hydrolyzing a glycoprotein containing a mucin-type sugar chain.

12. The method of claim 8 wherein the sugar acceptor is a peptide containing serine residue or threonine residue.

13. The method of claim 3 wherein the sugar donor is selected from the group consisting of alkylglycoside and arylglycoside.

14. The method of claim 13 wherein th sugar donor is the glycoside having a member, as an aglycon, selected from the group consisting fo para-nitrophenyl, ortho-nitrophenyl and benzyl.

15. The method of claim 3 wherein the sugar donor comprises a mixture of glycopeptides prepared by hydrolyzing a glycoprotein containing a mucin-type sugar chain.

16. The method of claim 3 wherein the sugar acceptor is a peptide containing serine residue or threonine residue.

* * * * *